(12) United States Patent
Greep et al.

(10) Patent No.: US 6,783,525 B2
(45) Date of Patent: *Aug. 31, 2004

(54) APPLICATION AND UTILIZATION OF A WATER-SOLUBLE POLYMER ON A SURFACE

(75) Inventors: Darcy W. Greep, South Jordan, UT (US); William G. Pitt, Orem, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/021,532

(22) Filed: Dec. 12, 2001

(65) Prior Publication Data

US 2003/0109864 A1 Jun. 12, 2003

(51) Int. Cl.[7] .............................................. A61B 18/18
(52) U.S. Cl. ........................................ 606/41; 606/45
(58) Field of Search .................................... 606/41–52

(56) References Cited

U.S. PATENT DOCUMENTS

| | | | | |
|---|---|---|---|---|
| 4,314,559 A | * | 2/1982 | Allen .......................... | 128/303 |
| 4,754,754 A | | 7/1988 | Garito et al. ........... | 128/303.14 |
| 4,785,807 A | | 11/1988 | Blanch .................. | 128/303.14 |
| 5,030,218 A | | 7/1991 | Alexander .................... | 606/45 |
| 5,197,962 A | * | 3/1993 | Sansom et al. ............... | 606/45 |
| 5,295,978 A | * | 3/1994 | Fan et al. .................... | 604/265 |
| 5,509,899 A | * | 4/1996 | Fan et al. .................... | 604/96 |
| 5,549,604 A | * | 8/1996 | Sutcu et al. .................... | 606/45 |
| 5,558,900 A | * | 9/1996 | Fan et al. .................. | 427/2.28 |
| 5,589,545 A | | 12/1996 | Ramachandran et al. ... | 525/184 |
| 5,702,387 A | | 12/1997 | Arts et al. ..................... | 606/45 |
| 5,713,895 A | * | 2/1998 | Lontine et al. ............... | 606/41 |
| 5,731,087 A | * | 3/1998 | Fan et al. .................... | 428/412 |
| 5,800,427 A | | 9/1998 | Zamba ........................ | 666/39 |
| 5,885,281 A | | 3/1999 | Urueta ........................ | 606/45 |
| 5,925,039 A | | 7/1999 | Landingham ................. | 606/41 |
| 5,925,043 A | | 7/1999 | Kumar et al. .................. | 606/45 |
| 6,106,523 A | * | 8/2000 | Morris ......................... | 606/45 |
| 6,132,427 A | * | 10/2000 | Jones et al. .................... | 606/45 |
| 6,139,547 A | * | 10/2000 | Lontine et al. ............... | 606/41 |
| 6,270,831 B2 | | 8/2001 | Kumar et al. .............. | 427/2.24 |
| 6,409,725 B1 | | 6/2002 | Khandkar et al. ............. | 606/45 |
| 6,544,596 B2 | | 4/2003 | Clemens et al. .......... | 427/407.1 |
| 6,551,267 B1 | | 4/2003 | Cohen et al. ............... | 604/6.15 |
| 6,558,686 B1 | | 5/2003 | Darouiche ................... | 424/423 |
| 6,558,798 B2 | | 5/2003 | Zhong et al. ................ | 428/420 |
| 6,559,132 B1 | | 5/2003 | Holmer ....................... | 514/56 |
| 2001/0031964 A1 | | 10/2001 | Gentelia et al. .............. | 606/45 |

OTHER PUBLICATIONS

Mikos, A.G. et al. "*Laminated Three–Dimensional Biodegradable Foams For Use In Tissue Engineering*", 1993, Biomaterials, vol. 14, No. 5, pp 323–330.

Ikada, Ph.D., Y. et al. "*Lubricious Polymer Surfaces*", 1993, Lubricating Polymer Surfaces, pp 41–71.

* cited by examiner

*Primary Examiner*—Michael Peffley
*Assistant Examiner*—Aaron Roane
(74) *Attorney, Agent, or Firm*—Workman Nydegger

(57) ABSTRACT

Methods, systems, and devices for applying and utilizing a water-soluble polymer on a surface to provide desirable properties, attributes and/or characteristics to the surface. In a first embodiment, the water-soluble polymer at least partially fills one or more pores of a fluoropolymer or a porous metal. In a second implementation, the water-soluble polymer is mixed into a base material and the mixture is applied as a coating layer onto the surface. Where the surface is an electrosurgical electrode tip, the desirable properties, attributes and/or characteristics may include the ability to attract water that assists in cooling and/or lubricating the tip, to create a low shear, sacrificial layer that protects and enhances the tip, to supply a radical scavenger or inhibitor that reduces damage at the tip, and/or to deposit factors, such as healing factors, from the tip onto one or more contact surfaces of the patient's body.

44 Claims, 4 Drawing Sheets

APPLICATION AND UTILIZATION OF A WATER-SOLUBLE POLYMER ON A SURFACE

RELATED PATENT APPLICATIONS

Reference is made to copending U.S. patent application Ser. No. 10/021,607, filed on Dec. 12, 2001, and entitled "Utilization of a Multi-Character Material in a Surface Coating of an Electrosurgical Instrument," the disclosure of which is incorporated by reference.

BACKGROUND OF THE INVENTION

1. The Field of the Invention

The present invention relates to the application and utilization of a water-soluble polymer on a surface. More specifically, the present invention relates to coating a surface with a water-soluble polymer, optionally together with a base material, to provide desirable properties, characteristics and/or attributes to the surface.

2. The Relevant Technology

The application of a polymer as a coating layer on a surface has proved to be a valuable asset in a variety of applications. One such application includes the use of a fluoropolymer, such as polytetrafluoroethylene ("PTFE"), as a coating layer of a surface. PTFE is a durable, chemically resistant, nonflammable thermoplastic substance that is widely used to coat a variety of surfaces including metal surfaces.

In the area of manufacturing pans for cooking, a fluoropolymer, such as a Teflon®, can be used as a non-stick coating layer. The non-stick layer facilitates the removal of food and other debris from the pan surface.

In the area of electrosurgery, fluoropolymers have been used to surface coat at least a portion of an electrosurgical tip to provide additional properties to the tip, including providing a non-stick surface and high temperature stability. Electrosurgery includes surgical procedures that use radio frequency (RF) electrical energy to cut tissue and/or cauterize leaking blood vessels. The RF energy is produced by a signal generator and is transmitted to an electrosurgical instrument, including a hand-piece and an electrode or tip, which is operated by a surgeon. The electrosurgical instrument delivers an electrical discharge to cellular matter of the patient's body adjacent to, adjoining with, contiguous with, or juxtaposed to the electrode. The discharge causes the cellular matter to heat up in order to cut tissue and/or cauterize blood vessels.

The high temperatures involved in electrosurgery can cause charred matter to form and become affixed to the electrode or tip of the electrosurgical instrument. The buildup of charred matter can reduce the efficiency of the cutting and/or cauterizing processes by creating an insulating barrier that interferes with the transference of RF energy to the targeted area. By way of example, when cauterizing an area to prevent bleeding, the charred matter can inhibit cauterization, cause the destruction of additional tissue and increase thermal tissue damage. Thus, buildup of the charred matter can slow the surgical procedure as the surgeon is required to remove the charred matter from the electrode or tip.

While the anti-adhesion properties of fluoropolymers that have been used to coat an electrode or tip of an electrosurgical instrument have facilitated electrosurgical cutting and/or cauterizing by reducing the buildup of debris on the electrode or tip, it has not completely eliminated such buildup. Accordingly, it would be an improvement in the art to augment or even replace the fluoropolymer coating with other anti-adhesion materials. Unfortunately, it has heretofore been difficult to adhere other materials to surfaces coated with a fluoropolymer because of anti-adhesion properties.

BRIEF SUMMARY OF THE INVENTION

The present invention relates to the application and utilization of a water-soluble polymer on a surface. More specifically, the present invention relates to coating a surface with a water-soluble polymer, optionally together with a base material, to provide desirable properties, characteristics and/or attributes to the surface.

Implementation of the present invention takes place in association with a surface, such as at least a portion of the surface of an electrosurgical electrode or tip of an electrosurgical instrument that may be used to cut tissue and/or cauterize blood vessels of a patient during a surgical operation. A non-stick surface is established on the electrode or tip to reduce the accumulation of charred blood and/or tissue, known as eschar, at the electrode or tip and to increase the efficiency of the electrode or tip in cutting tissue and/or cauterizing blood vessels. Moreover, the non-stick surface facilitates the removal of the eschar from the electrode or tip.

A water-soluble polymer may provide desired properties, attributes and/or characteristics to a surface. For example, when the surface is a portion of an electrode or tip of an electrosurgical instrument, the water-soluble polymer may attract water to the electrode or tip that assists in cooling and/or lubricating the electrode or tip. The water-soluble polymer may create a low shear, sacrificial layer on the electrode or tip that protects and enhances the performance of the tip. Alternatively or additionally, the water-soluble polymer may supply a radical scavenger or inhibitor to reduce damage to the electrode or tip, deposit factors, such as healing factors, from the electrode or tip onto one or more contact surfaces of the patient's body, or provide other desired properties, attributes and/or characteristics to the electrode or tip.

In one implementation of the present invention, a water-soluble polymer is advantageously used to at least partially fill one or more pores in a base material coating layer. Alternatively, the water-soluble polymer is used to at least partially fill one or more pores of a porous metal. In still another embodiment, the water-soluble polymer is used to at least partially fill cracks or voids formed in the substrate and/or cracks or voids formed in the base material coating layer. For example, in one embodiment, a process of electrophoresis is employed to draw the water-soluble polymer into the one or more pores, cracks, or voids to provide the desired properties, attributes and/or characteristics at the surface. An additional covering layer of the water-soluble polymer may optionally be applied over the base material coating layer or the substrate, such as a porous metal, to increase the desired properties, attributes and/or characteristics at the surface.

In another implementation, a water-soluble polymer is mixed into a base material, such as a silicone or ceramic, and a dip, brush, or spray process is employed to apply the mixture as a coating onto a surface to provide the desired properties, attributes and/or characteristics to the surface. As above, an additional covering layer of water-soluble polymer may optionally be applied over the mixture coating layer to increase the desired properties, attributes and/or characteristics at the surface.

While the methods and processes of the present invention have proven to be particularly useful in the area of electrosurgery, those skilled in the art can appreciate that the methods and processes can be used on a variety of different kinds of surfaces and in a variety of different areas of manufacture to yield a coated surface that has desired properties for performing a particular task.

Additional features and advantages of the present invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
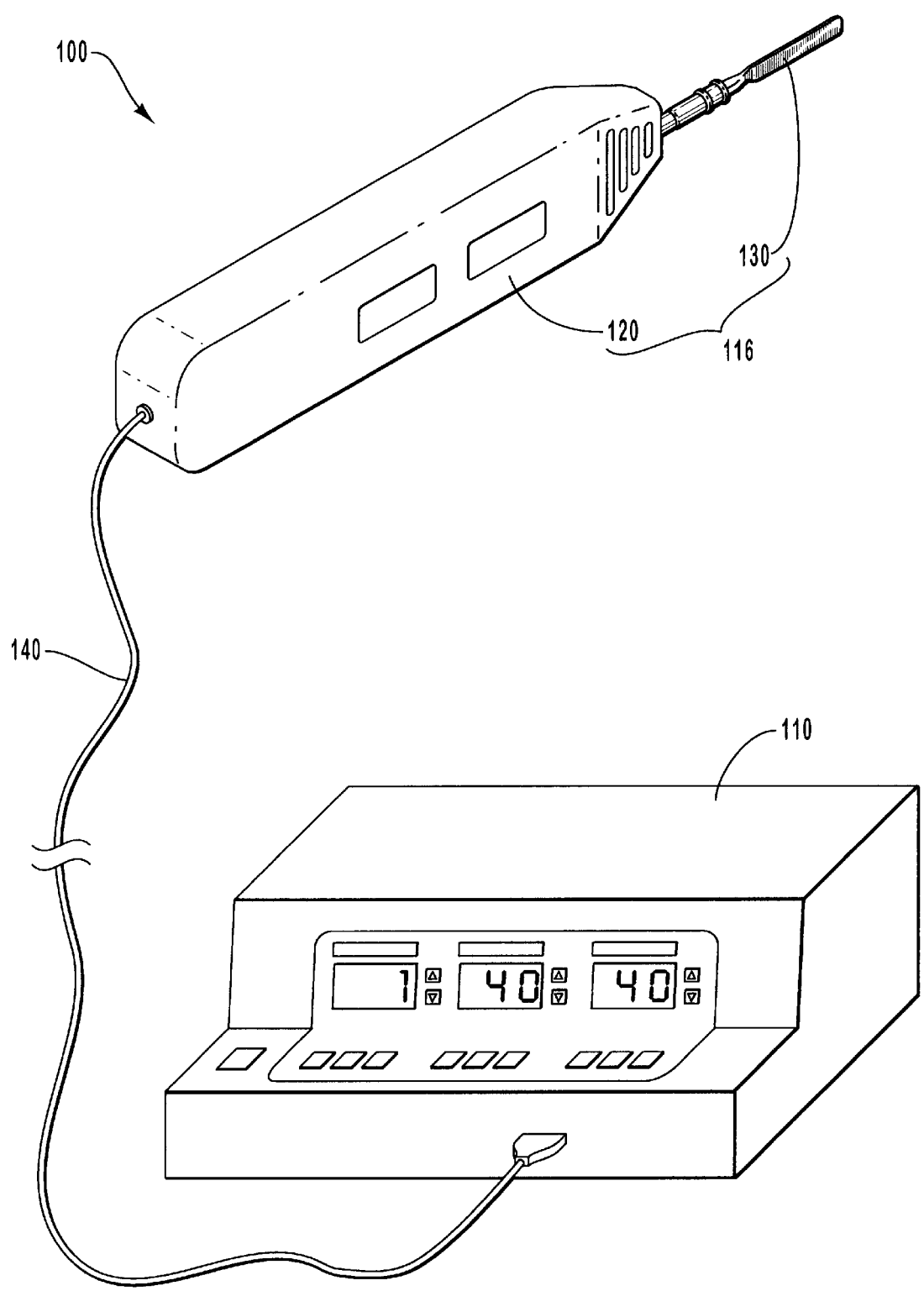
FIG. 1 illustrates an exemplary system that provides a suitable operating environment for use of the present invention.

The present invention relates to the application and utilization of a water-soluble polymer on a surface. More specifically, the present invention relates to coating a surface with a water-soluble polymer, optionally together with a base material, to provide desired properties, characteristics and/or attributes to the surface.

In the disclosure and in the claims the term "pore" shall refer to a cavity that is created or otherwise present in a base material. Moreover, the term "pore" shall include, but is not limited to, a channel, tunnel, interconnected pathway, crack, void, or other cavity in a base material and/or porous material. Furthermore, in the disclosure and in the claims the term "filled pore" shall refer to a collection of a material, such as a water-soluble polymer, that is produced by at least partially filling a pore with the material or by mixing the material with a base material and applying the mixture as a coating layer. Filled pores introduce desired properties, characteristics and/or attributes to a surface. Examples of desired properties include attracting water to the surface of an otherwise hydrophobic material to assist in cooling and/or lubricating the surface, creating a low shear, self-renewing, sacrificial layer of a surface that protects and enhances the surface, supplying a radical scavenger or inhibitor to a surface to reduce damage at the surface, depositing factors from a surface onto one or more contact surfaces, and the like.

In the disclosure, reference is made to the use of a fluoropolymer as a base material. In the disclosure and in the claims, the term "fluoropolymer" shall refer to a material that includes polymers that contain fluorocarbons or fluorinated hydrocarbons. By way of example, the term "Teflon®" represents a family of various fluoropolymers.

Reference is also made in the disclosure to particles of a "filler" that may be used to create pores in a base material coating layer. In the disclosure and in the claims the term "filler" shall refer to any polymer material that degrades thermally as the base material is cured, including non-aromatic hydrocarbon polymers. Examples of such filler polymers include polyethylene, polybutylene, polystyrene, polypropylene, and other thermally degrading materials. Additionally, the term "filler" refers to any solid or liquid organic material or solid salt that can be used to create pores in a base material coating layer. Illustratively, an example of a filler is an organic solid, liquid or gas that does not dissolve in the base material and which can be evaporated, burned off, or dissolved, such as, but not limited to sugar, wax, oils, fats, organic hydrocarbon liquids, freons, propane, butane, and other like materials. Similarly, an example of a filler is an inorganic solid, liquid or gas that does not dissolve in the base material and which can be evaporated, burned off, or dissolved, such as but not limited to, salt, silicone oils, carbon dioxide, air, argon and other like materials.

The following disclosure of the present invention is grouped into six subheadings, namely "Exemplary Operating Environment," "Creating Pores in a Coating Layer," "Filling Pores with a Water-Soluble Polymer," "Mixing a Water-Soluble Polymer with a Base Material," "Press Forming Pores into a Base Material," and "Creating Pores Without the Use of Filler Particles." The utilization of the subheadings is for convenience of the reader only and is not to be construed as limiting in any sense.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Exemplary Operating Environment

Figure 2A:
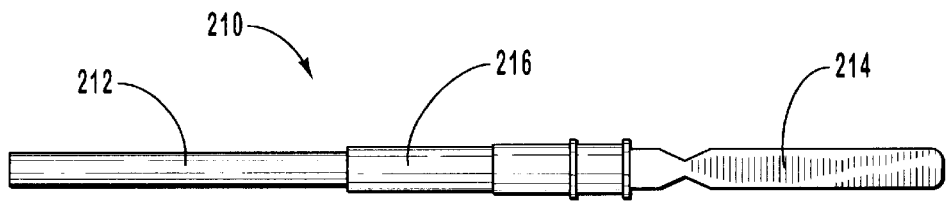
FIG. 2A illustrates an exemplary electrosurgical electrode or tip for use in the suitable operating environment of FIG. 1 to cut tissue and cauterize blood vessels in general surgery.
Figure 2B:
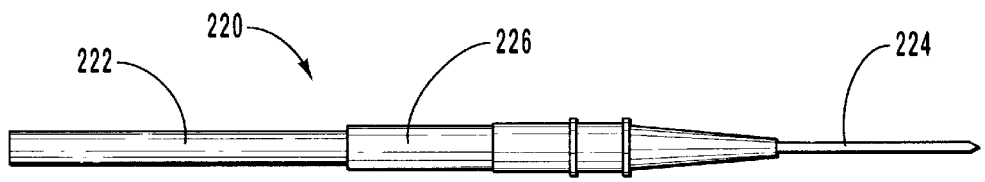
FIG. 2B illustrates an exemplary electrosurgical electrode or tip for use in the suitable operating environment of FIG. 1 to cut tissue and cauterize blood vessels in particularly dense areas.
Figure 2C:
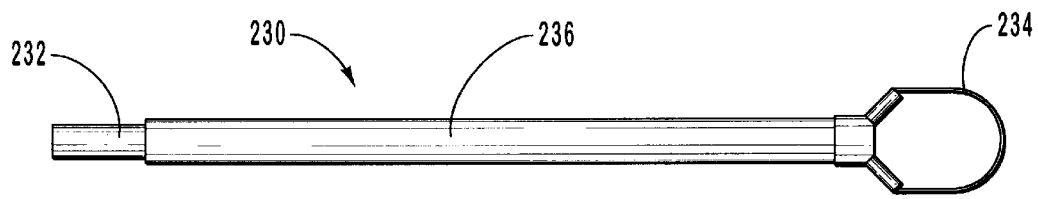
FIG. 2C illustrates an exemplary electrosurgical electrode or tip for use in the suitable operating environment of FIG. 1 to remove large sections of tissue.
Figure 2D:
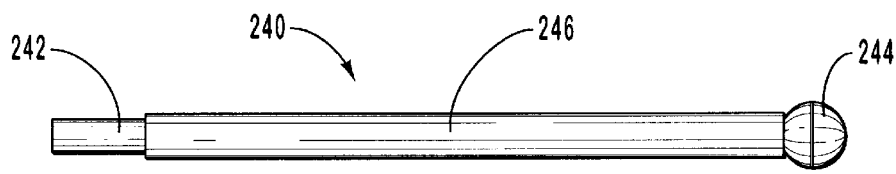
FIG. 2D illustrates an exemplary electrosurgical electrode or tip for use in the suitable operating environment of FIG. 1 to cauterize leaking blood vessels and to seal open structures.
Figure 2E:
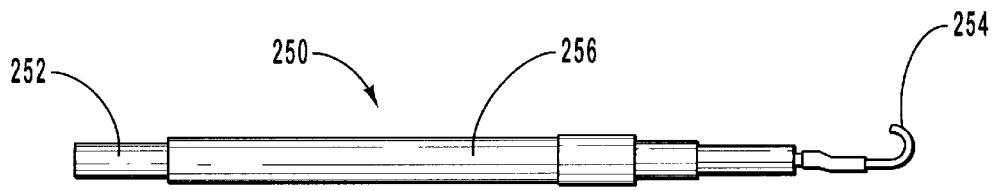
FIG. 2E illustrates an exemplary electrosurgical electrode or tip for use in the suitable operating environment of FIG. 1 to isolate tissue and to independently cut or cauterize.

FIGS. 1–2E and the corresponding discussion are intended to provide a brief, general description of a suitable operating environment in which the invention may be implemented. Although not required, the invention will be described in the general context of creating specific properties, attributes and/or characteristics on a surface area of electrode or tip of an electrosurgical instrument. Those skilled in the art, however, will appreciate that embodiments of the present invention may be practiced in association with a variety of different surfaces to create a variety of desirable properties, attributes and/or characteristics.

Referring to FIG. 1, an exemplary environment is illustrated that provides a suitable operating environment for use of the present invention. In FIG. 1, electrosurgical system 100 is illustrated, which includes a signal generator 110 and an electrosurgical instrument 116 electrically coupled to signal generator 110 though cord 140. A surgeon typically uses electrosurgical system 100 during surgical procedures to cut tissue and/or to cauterize blood vessels of a patient's body.

In electrosurgery, radio frequency (RF) electrical energy is produced by a signal generator, such as signal generator 110, and is introduced to a patient's body by electrosurgical instrument 116. More specifically, the radio frequency energy is introduced to the patient's body through an electrode or tip 130 electrically coupled to a hand-piece 120; the combination of electrode or tip 130 and hand piece 120 forms an exemplary electrosurgical instrument 116. The RF electrical energy generated by signal generator 110 is transmitted from signal generator 110 to electrode or tip 130 through hand-piece 120 and cord 140. An electrical discharge is delivered from tip 130 to the patient in order to cause the heating of cellular matter of the patient that is adjacent to, adjoining with, contiguous with, juxtaposed to, or in extremely close contact to tip 130. The heating takes place at an appropriately high temperature to allow performance of electrosurgery using hand piece 120 and electrode 130. A grounding electrode (not shown) may be employed to carry away any excess charge that dissipated into surrounding tissue of the patient's body.

During electrosurgery, electrode or tip 130 may be used to independently or concurrently cut and cauterize the patient's tissue. A constant sinusoidal signal supplied by signal generator 110 and transmitted to electrosurgical instrument 116 to allow tip 130 to cut through tissue of the patient's body. Alternatively, a damped wave signal supplied by signal generator 110 and transmitted electrosurgical instrument 116 allows tip 130 to cauterize leaking blood vessels. A combination of the constant sinusoidal signal and the damped wave signal can be supplied by signal generator 110 to tip 130 through hand piece 120 allowing tip 130 to concurrently cut and cauterize, thereby minimizing tissue trauma and blood loss during the surgical procedure.

FIGS. 2A–2E illustrate an exemplary assortment of interchangeable tips or electrodes for use with hand piece 120 to facilitate the acts of cutting tissue and/or cauterizing blood vessels. Each of the interchangeable tips or electrodes has a first end that can be coupled to hand piece 120, an insulator, and a second end that applies the discharge to the patient's body. The configuration of the second end allows for a great versatility of the acts of cutting and/or cauterizing in a variety of different surgical procedures. Although reference is made to interchangeable tips or electrodes, one skilled in the art can appreciate that alternate embodiments of the present invention can utilizes tips or electrodes that are attached to a hand piece and non-removable therefrom.

By way of example, FIG. 2A illustrates tip 210, which is a tip that may be used in general surgery for cutting tissue and for cauterizing blood vessels. End 212 is coupled to the hand piece 120 to allow the RF electrical energy, generated from the signal generator and transmitted to the hand piece 120, to be transmitted through tip 210. A discharge is delivered to the patient's body from end 214, which is in a blade-like configuration. End 214 has two parallel sides that are flat to allow end 214 to function in a similar manner as traditional scalpel. However, rather than employing a mechanical action for cutting through tissue, the electrical discharge allows end 214 to slide through the tissue as the tissue is being superheated to a high temperature. A coating 216, such as a base material coating layer and/or a water-soluble polymer layer, surrounds at least a portion of tip 210 and acts as an insulator.

Similarly, FIG. 2B illustrates tip 220, which may be used for cutting tissue and cauterizing leaking blood vessels in particularly dense areas of a patient's body, such as those experienced in cerebral operations. End 222 is adapted to couple to hand piece 120 to allow the RF electrical energy, generated from the signal generator and transmitted to and/or through hand piece 120, to be transmitted through tip 220. A discharge is delivered to the patient's body from end 224, which is in a needle-like configuration that comes to a point to allow for very accurate surgical procedures in dense areas of the patient's body. A coating 226, such as a base material coating layer and/or a water-soluble polymer layer, surrounds at least a portion of tip 220 and acts as an insulator. Through the use of tip 220, delicate cerebral tissues can be accurately removed with virtually no damage to any surrounding membranes and with minimal bleeding and/or swelling resulting from the procedure.

FIG. 2C illustrates tip 230, which may be used for the removal of large sections of tissue, as in, for example, prostate and tumor excision. End 232 is adapted to couple to the hand piece 120 to allow the RF electrical energy to be transmitted to or through tip 230. A discharge is delivered to the patient's body from end 234, which is in a loop-like configuration. A coating 236, such as a base material coating layer and/or a water-soluble polymer layer, surrounds at least a portion of tip 230 and acts as an insulator.

FIG. 2D illustrates tip 240, which may be used to specifically cauterize leaking blood vessels and to seal open structures. End 242 is adapted to couple to hand piece 120 to allow the RF electrical energy to be transmitted to or through tip 240. A discharge is delivered to the patient's body from end 244, which is in a spherical configuration. A coating 246, such as a base material coating layer and/or a water-soluble polymer layer, surrounds at least a portion of tip 240 and acts as an insulator.

FIG. 2E illustrates tip 250, which may facilitate a surgeon in reducing extraneous tissue damage by allowing individual tissues or blood vessels to be isolated and independently cut and/or cauterized. End 252 is adapted to couple to hand piece 120 to allow the RF electrical energy from the signal generator to be transmitted to or through tip 250. A discharge is delivered to the patient's body from end 254, which is in a hook-like configuration. A coating 256, such as a base material coating layer and/or a water-soluble polymer layer, surrounds at least a portion of tip 250 and acts as an insulator.

Ends 214, 224, 234, 244 and 254 are examples of surfaces upon which a coating layer may be applied to render one or more desirable attributes and/or properties. When the surface is at least a portion of an electrode or tip, an example of a desired property includes minimizing the amount of eschar that accumulates on the electrosurgical electrode or tip. The minimization of eschar allows for a more efficient use of the electrode or tip by reducing damage to surrounding tissues that may have been otherwise caused by an accumulation of eschar during an electrosurgical procedure.

Creating Pores in a Coating Layer

At times, it is advantageous to create pores in a coating layer of a surface or substrate. For example, when the coating layer of a surface comprises a material having an anti-adhesion property, such as a fluoropolymer, and another material, such as a water-soluble polymer, is to be applied to the coating layer, it is advantageous to create pores in the coating layer to improve the adhesion of the applied material to the coating layer. Thus, the following provides an exemplary explanation as to the creation of pores in a coating layer.

In one embodiment of the present invention, the base material used to coat at least a portion of a surface is a fluoropolymer, such as polytetrafluoroethylene ("PTFE") or Teflon®. The base material coating provides a non-stick coating, which has heretofore been difficult to adhere other materials thereto because of the anti-adhesion properties of the fluoropolymer. Pores are created in the base coating layer by inserting desirably sized small particles of a filler into the base material prior to applying it onto a surface, such as at least a portion of the surface area of a conductive electrosurgical tip.

Figure 3A:
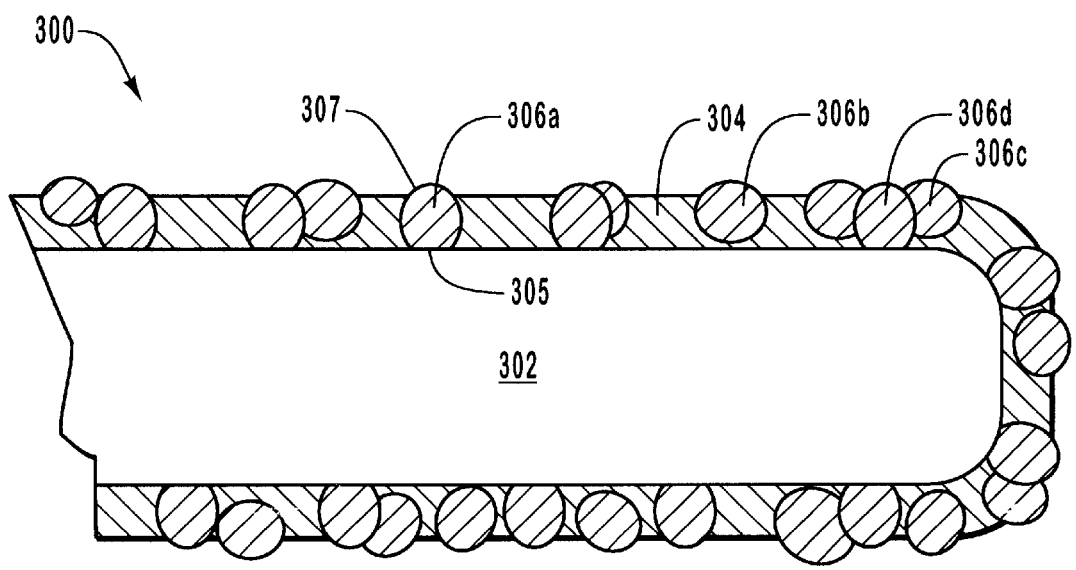
FIG. 3A illustrates an exemplary cross-sectional view of an electrosurgical electrode or tip that has a coating layer applied thereon, wherein the coating layer comprises a base material and one or more particles mixed into the base material.

With reference to FIG. 3A, a tip of an electrosurgical electrode or tip is illustrated as electrode or tip 300, which includes a substrate 302. The substrate 302 is configured to conduct RF energy and can be fabricated from various materials or combinations of materials to facilitate conducting RF energy. Illustratively, substrate 302 can be metallic, such as surgical stainless steel, a combination of metallic and non-metallic materials, or the like. Prior to applying a coating layer, the surface of substrate 302 may be prepared by being heat cleaned to remove any oils or contaminants and may be roughened to provide a footing for the coating layer.

Once the surface of substrate 302 is prepared through the processes of heat cleaning and roughening, a suspension of base material particles mixed with particles of a filler and an etching agent is spray coated onto the substrate 302 so as to uniformly apply a coating layer to at least a portion of substrate 302. The etching agent improves the bond between the base material coating layer 304 and the substrate 302. Although reference is made to creating a suspension of the base material particles mixed with particles of a filler and an etching agent, it can be appreciated by one skilled in the art that an emulsion of the base material particles mixed with particles of a filler and an etching agent can also be used.

In FIG. 3A, the coating layer applied on substrate 302 is illustrated as including a plurality of desirably sized particles 306 of a filler that are within the base material coating layer 304. In one embodiment, where it is advantageous to have the pores extend through the base material to the metal substrate 302, the thickness of the coating layer applied onto substrate 302 should approximately correspond to the diameter of the particles by the thickness being e.g., equal to or smaller than the diameter of the particles of filler. Therefore, as illustrated in FIG. 3A, a portion of a first end 305 of particle 306a may be in abutting contact with the surface of the substrate 302 and a portion of an opposing end 307 of particle 306a is exposed within the top surface of the coating layer. Alternatively, other embodiments of the present invention do not require that the pores extend through the base material to the substrate, thus particles are included in the base material coating layer that are not in abutting contact with the substrate, as illustrated by particle 306b. Furthermore, embodiments embrace the combination of pores created that extend through the base material to the substrate and pores that do not extend through to the substrate. Thus, as illustrated in FIG. 3A, a combination of particles that are in abutting contact with a substrate 302 and particles that are not in abutting contact with the substrate 302 may be located in the base material coating layer 304. Alternatively or additionally, particles that do not extend through to the substrate may be in contact with particles that do contact the substrate 302. This is illustrated, for example, by particle 306c, which is in abutting contact with a particle 306d that is in abutting contact with substrate 302. While the particles 306 illustrated in FIG. 3A are generally oval in shape and similar in size, the particles of filler may have a variety of different shapes and/or sizes, as will be appreciated by those skilled in the art.

Once the coating layer has been applied to substrate 302, a drying process may be employed under controlled humidity to remove, for example, a solvent or etchant material. The tip may then be placed in an oven and heated to evaporate, remove, or drive off the water or other solvent from the tip. The temperature may then be increased to thermally degrade the filler, to remove the particles 306 from the base material coating layer 304 and the oven is brought to a sintering temperature.

Figure 3B:
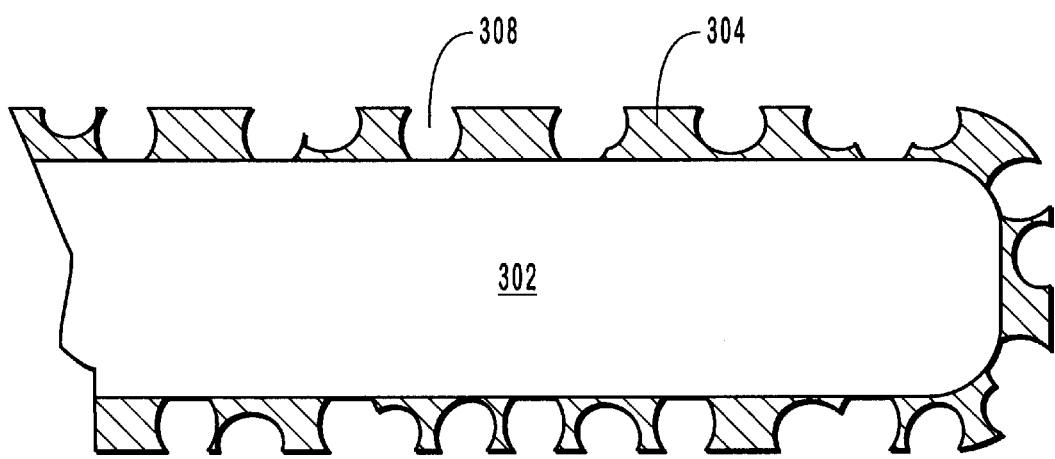
FIG. 3B illustrates an exemplary cross-sectional view of the electrode or tip of FIG. 3A after the tip has gone through a sintering process to burn off the one or more particles from the base material, leaving pores that extend through the base material to the surface.

FIG. 3B illustrates the electrosurgical tip after having been subject to the sintering process, which evaporates any carrier liquid remaining from the spray up, coating or etching material, which may be the first to evaporate from the tip. The sintering process also causes the base material to enter into any cracks located on the surface of substrate 302 and coalesces any remaining particles of the base material. As provided above, the sintering process further causes the thermal degradation of the filler and causes evaporation of the degradation products so as to create pores in the coating layer, where once particles occupied a location within the coating layer.

In FIG. 3B, a plurality of pores are illustrated, such as pore 308, that extend into and/or through the base material coating layer to cause the coating layer to be porous. The size of the pores corresponds to the size of the particles of filler that were originally selected for inclusion into the base material paint. Thereafter, the pores formed in the coating layer can be filled with one or more materials, such as water-soluble polymers to create filled pores that provide desired properties, attributes and/or characteristics to the coated surface, as will be further explained below.

Filling Pores with a Water-Soluble Polymer

Embodiments of the present invention allow one or more materials having desirable properties, attributes and/or characteristics to be applied to the coating layer having pores created therein. One such material is a water-soluble polymer, such as polyethylene oxide, that may be used to partially fill at least one or more of the pores created in the coating layer. When the pores are created to extend through the coating layer to the surface or substrate, the water-soluble polymer may adhere directly onto the substrate. Optionally, a second coating layer may be applied that coats the original coating layer and adheres to the material used to fill the pores.

Figure 3C:
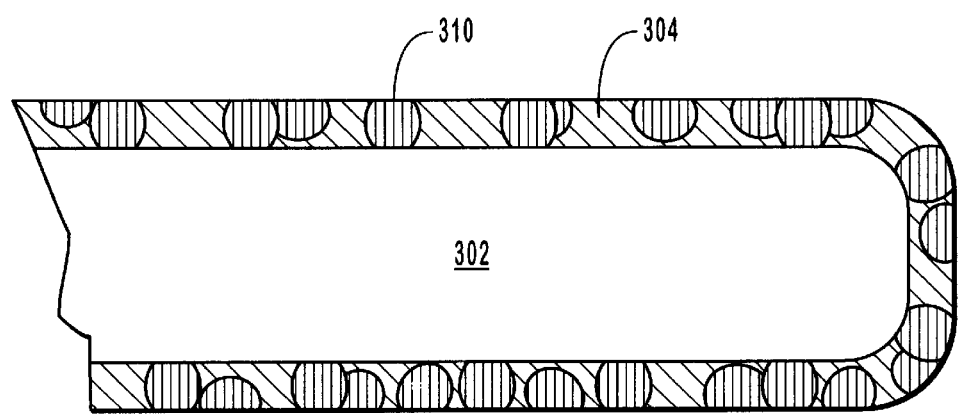
FIG. 3C illustrates an exemplary cross-sectional view of the electrode or tip of FIG. 3B, where the pores are filled with a water-soluble polymer to form filled pores that extend through the base material to the surface of the electrosurgical tip and provide desired properties to the coating layer.

Pores, such as pore 308 of FIG. 3B, may be filled with a water-soluble polymer to provide filled pores, such as filled pore 310 of FIG. 3C, that provide desired properties, attributes and/or characteristics to the surface. The filled pores are illustrated in FIG. 3C as being interspersed within a base material coating layer 304 on substrate 302. Examples of the water-soluble polymers that may be used to form filled pores includes polyethylene oxide ("PEO"), polyethylene glycol ("PEG"), a copolymer of ethylene oxide, and the like. Alternatively, the water-soluble polymer can include a water soluble acrylate polymer, such as polymers or copolymers of hydroxyethyl methacrylate, a water soluble acrylic acid polymer, such as polymers or copolymers of methacrylic acid, a water soluble vinyl polymer, such as polymers or copolymers of poly(vinyl alcohol), a water soluble hetero atom polymer (or water soluble heterochain polymer), such as polymers or copolymers of polyesters or polyamides such as polylysine, polyethylene oxide ("PEO"), polyethylene glycol ("PEG"), polyethylene oxide-poly(dimethylsiloxane) copolymer ("PEO-PDMS"), other copolymers of ethylene oxide, polylactone, polycaprolactone, other caprolactone copolymers, water soluble nylon, ethylene maleic anhydride copolymer and other maleic anhydrides, ionene (ionic amine) polymers, polyalkylene oxalate, or the like, a water soluble natural polymer and derivative thereof such as starch, gelatin, other proteins, chitin-poly(N-acetyl-D-glucosamine) and derivatives, hyaluronic acid and salts thereof, other polysaccharides, chondritic sulfate, agarose, methylcellulose, ethylcellulose, hydroxyethylcellulose, hydroxypropyl-methylcellulose, ethyl-hydroxyethylcellulose, ethyl-methylcellulose, hydroxyethyl-methylcellulose, carboxymethylcellulose and salts thereof, carboxymethylhydroxyethylcellulose salts, other cellulosic derivatives. In addition to the above, other applicable polymers are disclosed in co-pending U.S. patent application Ser. No. 10/021,607, entitled "Utilization of a Multi-Character Material in a Surface Coating of an Electrosurgical Instrument," the disclosure of which is incorporated herein by reference.

The pores may be filled by a variety of processes, including the acts of adsorption from solution or vapor, spraying, wiping, brushing, or other methods to apply the water-soluble polymer into at least a portion of the created pores. In one embodiment, the pores are filled with a water-soluble polymer through the process of electrophoresis to provide the desirable properties, attributes and/or characteristics to the tip.

Electrophoresis is the movement of electrically charged particles through or along a medium as a result of an electric field formed between electrodes immersed in the medium. In this process, a charge may be added to one or both ends of a water-soluble polymer molecule or any location intermediate of the ends of the water-soluble polymer molecule. The charged molecule is then electrophoresed using an electric field to attract the water-soluble polymer molecules to enter the pores created in the base material, resulting in filled pores, such as filled pore 310 of FIG. 3C, that are interspersed in the base material coating layer 304.

In another embodiment of the present invention, rather than creating pores in a coating layer, the substrate of the electrosurgical electrode or tip comprises a metal that is porous or includes voids or cracks in the surface thereof. As such, one or more of the pores, voids, or cracks of the metal are at least partially filled with the water-soluble polymer to provide the desirable properties, attributes and/or characteristics to the surface. Illustratively, the process of electrophoresis may be employed to attract the water-soluble polymer molecules to enter pores, voids, or cracks of the metal, resulting in filled pores, or filled voids or cracks, located at the substrate of the electrode or tip that are interspersed by the metal. Other application processes may alternatively be employed to partially and/or completely fill the pores, voids, or cracks with the water-soluble polymer, including the acts of adsorption from solution or vapor, spraying, wiping, brushing, or other methods to partially or completely fill the pores, voids, and/or cracks.

Mixing a Water-Soluble Polymer with a Base Material

While the embodiments discussed above disclose creating and/or using pores, cracks, or voids in a coating layer or the substrate that are at least partially filled with a water-soluble polymer to provide desirable properties, characteristics and/or attributes to a surface, embodiments of the present invention embrace other methods for applying a water-soluble polymer to a surface. For example, in one embodiment particles of the water-soluble polymer are mixed directly into a base material prior to the mixture being applied as a coating layer on a surface.

By way of example, a base material that may be used is silicone, room temperature curing silicone, ceramic, such as sol ceramic, or the like, and a water-soluble polymer that may be used is PEO, PEG, a copolymer of ethylene oxide, or other water-soluble polymers described herein or known to one skilled in the art in light of the teaching contained herein. The water-soluble polymer particles are mixed directly into a liquid, semi-liquid, or gel base material and the mixture is applied to a surface, such as an electrosurgical electrode or tip, through the use of a dip, brush, or spray process. It can be understood by one skilled in the art that elevated temperatures are not required to cure the coating layer applied to the electrosurgical electrode or tip, rather materials that cure at room temperature can be included in the coating layer. The presence of the water-soluble polymer collections in the coating layer may function in a similar manner as the filled pores discussed above to provide desirable properties, characteristics and/or attributes to the surface.

Thus, as discussed herein, the embodiments of the present invention embrace the application and utilization of a water-soluble polymer on a surface. The presence of the water-soluble polymer introduces many desirable properties, characteristics and/or attributes to the surface. By way of example, when the surface is an electrosurgical electrode or tip, adding a water-soluble polymer to a base material typically causes an attraction of water to the surface, even when the surface may otherwise be hydrophobic, such as when the surface includes a fluoropolymer coating. The attraction of water may assist in cooling the electrode or tip by evaporation during use of the electrode or tip, thereby protecting and prolonging the service life of the base material on the electrode or tip. The attraction of water may also act as a lubricant for an enhanced release character of the base material. The presence of the water-soluble polymer in a base material coating layer may also provide a low shear, sacrificial layer during electrode or tip cleaning that can serve to protect and enhance the activity of the base material. The water-soluble polymer may also act to provide a radical scavenger or inhibitor to reduce damage done to the base material during a process of gamma sterilization, thereby improving the properties and service life of the base material. Furthermore, the water-soluble polymer may act as a carrier of antibiotic factors, healing factors, anti-adhesion factors, anti-tumor factors, tumor necrosis factors, and the like, which are specifically included in the coating of the electrode or tip as desired, and by design, for deposition in and on tissues of a patient's body where electrosurgical procedures are performed.

Figure 4:
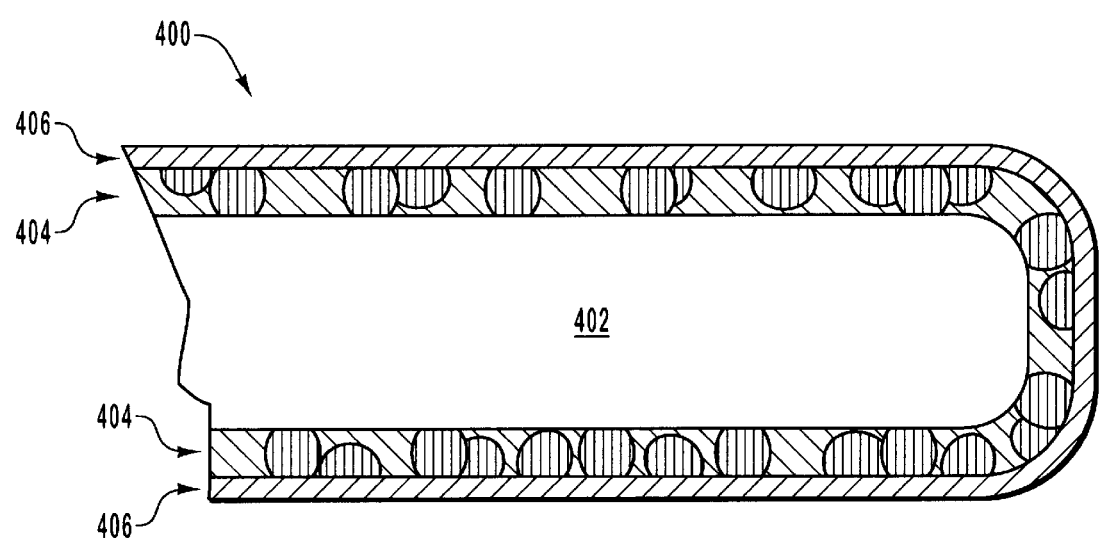
FIG. 4 illustrates an exemplary cross-sectional view of an electrosurgical electrode or tip that has a first coating layer comprising a water-soluble polymer and a base material, and a second layer comprising a water-soluble polymer.

Embodiments of the present invention embrace the application of a second coating layer over the original coating layer to increase the desired properties, attributes and/or characteristics at the electrode or tip, such as electrode or tip 400. This is illustrated in FIG. 4, which provides a substrate 402 having a coating layer 404 that comprises a base material such as a fluoropolymer and one or more filled pores of a water-soluble polymer that are interspersed in the base material. Furthermore, a second layer 406 of a material, such as a water-soluble polymer or other material, is applied over the coating layer 404 to increase the desired properties, attributes and/or characteristics of the electrode or tip. Thus, where a second layer is applied, the material used to fill the pores in the coating layer 404 assists in bonding the second layer 406 to the substrate 402 even when an anti-adhesive material, such as an anti-adhesive fluoropolymer, is located therebetween.

Press Forming Pores into a Base Material

As discussed above, it is advantageous to create pores in a coating layer of a surface or substrate. For example, when the coating layer of a surface comprises a material having an anti-adhesion property, such as a fluoropolymer, and another material, such as a water-soluble polymer, is to be applied to the coating layer, it is advantageous to create pores in the coating layer to improve the adhesion of the applied material to the coating layer. Although reference is made to creating pores in the base coating layer by removing a filler from a coating layer subsequent to applying the mixture of filler and coating layer to the electrosurgical electrode or tip, methods and processes are provided for forming pores in the base material coating layer through pressing filler particles into an uncured or partially cured base material coating layer.

Generally, as with other embodiments of the present invention, a suspension or emulsion of base material particles, such as a fluoropolymer, such as polytetrafluoroethylene ("PTFE") or Teflon®, mixed with an etching agent is spray coated onto a substrate, such as substrate 302 of electrosurgical electrode or tip 120.

In one embodiment, the suspension or emulsion is partially cured through partially performing a drying process to partially remove, for example, the solvent or etchant material. Following partially curing the base material coating layer, particles of a filler are pressed into the surface of the base material coating layer. Alternatively, the partially cured base material coating layer is pressed into filler particles. In either case, the base material coating layer, including filler, may then be placed in an oven and heated to evaporate, remove, or drive-off the water from the tip. The temperature may then be increased to thermally degrade the filler, to remove the filler particles from the base material coating layer. Consequently, the base material coating layer becomes formed with the pores. As with earlier described embodiments, a sintering process and additional layer processes can be performed to the base material coating layer and/or the tip of the electrosurgical instrument.

In another embodiment, a room temperature curable material is used as the base material coating layer. In such a case, the base material coating layer is applied to the substrate and the partially cured base material coating layer is pressed into particles of a filler, rather than pressing the filler into the base material coating layer.

In still another embodiment, whether using a base material coating layer curable at room temperature or at temperatures greater than room temperature, the partially cured base material coating layer is dusted with the filler. The filler is removed through a dissolving process, whether or not the dissolving process occurs before or after substantially completely curing the base material coating layer. When the filler is dissolved, the base material coating layer is formed with pores to receive the water-soluble polymer.

Creating Pores Without the Use of Filler Particles

As discussed above, it is advantageous to create pores in a coating layer of a surface or substrate. For example, when the coating layer of a surface comprises a material having an anti-adhesion property, such as a fluoropolymer, and another material, such as a water-soluble polymer, is to be applied to the coating layer, it is advantageous to create pores in the coating layer to improve the adhesion of the applied material to the coating layer. Although reference is made to creating pores in the base coating layer by removing a filler from a coating layer subsequent to applying the mixture of filler and coating layer to the electrosurgical electrode or tip, methods and processes are known to create pores, cracks, or voids within the coating layer without use of a filler.

As discussed herein, a suspension or emulsion of base material particles, such as a fluoropolymer, such as polytetrafluoroethylene ("PTFE") or Teflon®, mixed with an etching agent is spray coated onto a substrate, such as substrate 302. The spraying process enables a uniform application of the base material coating layer to at least a portion of the substrate. The etching agent including in the suspension improves the bond between the base material coating layer and the substrate.

According to this embodiment of the present invention, the sprayed mixture is devoid of filler particles that are used to generate or create pores in the base material coating layer to aid with the adhesion of subsequently layers applied to base material coating layer. Instead of using filler particles, the present invention utilizes the curing characteristics of the base material coating layer. Specifically, as a drying process is employed to remove the solvent or etchant material, i.e., the solvent or etchant material is evaporated, cracks and voids are formed in the base material coating layer. Changing the curing characteristics of the base material coating layer varies the size of the cracks and voids formed in the base material coating layer. For instance, curing of the base material coating layer faster than is typically acceptable for the base material may create larger cracks and voids than when the curing is performed more slowly or in accordance with instructions provided by the manufacturer of the base material coating layer. As this implies, differently sized cracks and voids form in the base material coating layer, even when the base material coating layer is cured using acceptable temperatures, times, and pressures for the specific base material. These cracks and voids, whether created through acceptable or typically unacceptable curing principles and techniques for the base material, act like pores that facilitate adhesion of subsequent layers to the base material coating layer.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for coating a tip of an electrosurgical instrument, the method comprising the acts of:
    applying a base material to a tip of an electrosurgical instrument;
    applying a first layer of a water-soluble polymer to the tip and interspersed within the base material, the water-soluble polymer providing a low shear, sacrificial layer to the tip; and
    applying a second layer of the water-soluble polymer onto the first layer.

2. A method as recited in claim 1, wherein the base material includes one or more pores therein.

3. A method as recited in claim 2, wherein the act of applying a the first layer of the water-soluble polymer comprises the act of using electrophoresis to draw the water-soluble polymer into at least a portion of the one or more pores.

4. A method as recited in claim 2, wherein the act of applying applying a first layer of the water-soluble polymer comprises using at least one of:
    (i) a dip process;
    (ii) a spray process;
    (iii) a brush process;
    (iv) a wiping process; or
    (v) an adsorption process.

5. A method as recited in claim 1, wherein the base material comprises a fluoropolymer.

6. A method as recited in claim 1, further comprising the act of mixing the water-soluble polymer of the first layer and the base material, wherein the mixing is performed prior to applying, and wherein applying the base material and applying the water-soluble polymer are performed by using a process to apply the mixture of the water-soluble polymer and the base material to the tip.

7. A method as recited in claim 6, wherein the process used to apply the mixture comprises at least one of:
    (i) a dip process;
    (ii) a brush process; or
    (iii) a spray process.

8. A method as recited in claim 1, wherein the base material comprises at least one of:
    (i) a silicone;
    (ii) a ceramic; or
    (iii) a glass.

9. A method as recited in claim 1, wherein the water-soluble polymer comprises at least one of:
    (i) polyethylene oxide;
    (ii) polyethylene glycol; or
    (iii) a copolymer of ethylene oxide.

10. A method as recited in claim 1, wherein the water-soluble polymer comprises at least one of a water soluble acrylate polymer, a water soluble acrylic acid polymer, a water soluble vinyl polymer, a water soluble hetero atom polymer, and a water soluble natural polymer.

11. A method as recited in claim 1, wherein the water-soluble polymer comprises polymers or copolymers of hydroxyethyl methacrylate.

12. A method as recited in claim 1, wherein the water-soluble polymer comprises polymers or copolymers of methacrylic acid.

13. A method as recited in claim 1, wherein the water-soluble polymer comprises polymers or copolymers of poly (vinyl alcohol).

14. A method as recited in claim 1, wherein the water-soluble polymer comprises polymers or copolymers of polylysine.

15. A method as recited in claim 1, wherein the water-soluble polymer comprises a hyaluronic acid or derivative of hyaluronic acid.

16. A method as recited in claim 1, wherein the water-soluble polymer is a carrier that deposits a factor on a patient's body during an electrosurgical procedure.

17. A method as recited in claim 16, wherein the factor deposited is at least one of:
    (i) an antibiotic factor;
    (ii) a healing factor;
    (iii) an anti-adhesion factor;
    (iv) an anti-tumor factor; or
    (v) a tumor necrosis factor.

18. A method as recited in claim 1, further comprising an act of forming one or more pores in the base material.

19. A method for coating a tip of an electrosurgical instrument, the method comprising the acts of:
    applying a base material to a tip of an electrosurgical instrument;
    forming one or more pores in the base material; and
    applying a water-soluble polymer to the tip;
    wherein the act of forming one or more pores in the base material comprises:
        partially curing the base material;
        pressing a filler into the partially cured base material; and
        removing the filler to leave one or more pores in the base material.

20. A method as recited in claim 19, wherein the act of removing the filler comprises removing the filler through a process selected from the group consisting of a heating process and a dissolving process.

21. A method for coating a tip of an electrosurgical instrument, the method comprising the acts of:
    applying a base material to a tip of an electrosurgical instrument;
    forming one or more pores in the base material; and
    applying a water-soluble polymer to the tip;
    wherein the act of forming one or more pores in the base material comprises:
        partially curing the base material;
        pressing the partially cured base material into a filler; and
        removing the filler to leave one or more pores in the base material.

22. A method as recited in claim 4, wherein the act of removing the filler comprises removing the filler through a process selected from the group consisting of a heating process and a dissolving process.

23. A method for coating a tip of an electrosurgical instrument, the method comprising the acts of:
    applying a base material to a tip of an electrosurgical instrument
    forming one or more pores in the base material; and
    applying a water-soluble polymer to the tip;
    wherein the act of forming one or more pores in the base material comprises curing the base material to cause cracks, voids, or pores to be formed in the base material.

24. A method for coating a tip of an electrosurgical instrument, the method comprising:
applying a base material to a tip of an electrosurgical instrument;
applying a first layer of a water-soluble polymer interspersed within the base material; and
applying a second layer of a water-soluble polymer over the first layer.

25. A method for coating a tip of an electrosurgical instrument, the method comprising:
applying a base material to a tip of an electrosurgical instrument, the base material including one or more pores therein; and
applying a water-soluble polymer over the base material, wherein applying the water-soluble polymer comprises using electrophoresis to draw the water-soluble polymer into at least a portion of the one or more pores, wherein the combination of the water-soluble polymer and the base material form a first layer about at least a portion of the tip.

26. A method as recited in claim 25, further comprising applying a second layer of a water-soluble polymer over the first layer.

27. A method for coating a tip of an electrosurgical instrument, the method comprising:
mixing a water-soluble polymer and a base material; and
applying the mixture of the water-soluble polymer and the base material to a tip of an electrosurgical instrument.

28. A method as recited in claim 27, wherein applying the mixture comprises at least one of:
a dip process;
a brush process; or
a spray process.

29. A tip for use in performing an electrosurgical procedure, the tip comprising:
a substrate;
a base material over the substrate;
a first layer of a water-soluble polymer interspersed within the base material; and
a second layer of a water-soluble polymer over the first layer.

30. A tip as recited in claim 29, wherein the water-soluble polymer comprises at least one of:
(i) polyethylene oxide;
(ii) polyethylene glycol; or
(iii) a copolymer of ethylene oxide.

31. A tip as recited in claim 29, wherein the water-soluble polymer comprises at least one of a water soluble acrylate polymer, a water soluble acrylic acid polymer, a water soluble vinyl polymer, a water soluble hetero atom polymer, and a water soluble natural polymer.

32. A tip as recited in claim 29, wherein the water-soluble polymer comprises polymers or copolymers of hydroxyethyl methacrylate.

33. A tip as recited in claim 29, wherein the water-soluble acid polymer comprises polymers or copolymers of methacrylic acid.

34. A tip as recited in claim 29, wherein the water-soluble polymer comprises polymers or copolymers of poly(vinyl alcohol).

35. A tip as recited in claim 29, wherein the water-soluble polymer comprises polymers or copolymers of polylysine.

36. A tip as recited in claim 29, wherein the water-soluble polymer comprises a hyaluronic acid or derivative of hyaluronic acid.

37. A tip as recited in claim 29, wherein the substrate includes a porous metal.

38. A tip as recited in claim 29, wherein the substrate includes surgical stainless steel.

39. A tip as recited in claim 29, wherein the substrate includes roughened metal.

40. A tip as recited in claim 29, wherein the water-soluble polymer provides a radical scavenger that reduces damage to the base material during a process of gamma sterilization.

41. A tip as recited in claim 29, wherein the coating further includes comprising an etching agent.

42. A tip as recited in claim 29, wherein the base material comprises at least one of:
(i) a fluoropolymer;
(iv) a silicone;
(ii) a ceramic; or
(iii) a glass.

43. A tip as recited in claim 29, wherein the water-soluble polymer is a carrier that deposits a factor on a patient during an electrosurgical procedure.

44. A tip as recited in claim 29, wherein the factor comprises at least one of:
(i) an antibiotic factor;
(ii) a healing factor;
(iii) an anti-adhesion factor;
(iv) an anti-tumor factor; or
(v) a tumor necrosis factor.

* * * * *

UNITED STATES PATENT AND TRADEMARK OFFICE
CERTIFICATE OF CORRECTION

PATENT NO. : 6,783,525 B2
DATED : August 31, 2004
INVENTOR(S) : Darcy W. Greep

It is certified that error appears in the above-identified patent and that said Letters Patent is hereby corrected as shown below:

Column 5,
Line 19, before "electrode or tip" insert -- an --
Line 51, before "dissipated" insert -- has --
Line 55, after "sinusoidal signal" insert -- is --
Line 59, before "electrosurgical instrument" insert -- to --

Column 6,
Line 10, before "tips or electrodes" change "utilizes" to -- utilize --
Line 21, before "traditional scalpel" insert -- a --

Column 9,
Line 18, before "polyethylene oxide" change "includes" to -- include --

Column 11,
Line 64, after "the filler," insert -- and --

Column 12,
Line 40, after "The etching agent" change "including" to -- included --
Line 47, before "base material" insert -- the --

Column 13,
Line 24, before "the first layer" remove "a"

Column 14,
Line 60, after "instrument" insert -- ; --

UNITED STATES PATENT AND TRADEMARK OFFICE
CERTIFICATE OF CORRECTION

PATENT NO. : 6,783,525 B2
DATED : August 31, 2004
INVENTOR(S) : Darcy W. Greep

It is certified that error appears in the above-identified patent and that said Letters Patent is hereby corrected as shown below:

Column 16,
Line 29, after "in claim 29," remove "wherein the coating"
Line 30, before "comprising" remove "includes"

Signed and Sealed this

Twenty-second Day of March, 2005

JON W. DUDAS
*Director of the United States Patent and Trademark Office*